(12) United States Patent
Burkett et al.

(10) Patent No.: US 6,511,503 B1
(45) Date of Patent: Jan. 28, 2003

(54) CATHETER APPARATUS FOR TREATING OCCLUDED VESSELS AND FILTERING EMBOLIC DEBRIS AND METHOD OF USE

(75) Inventors: David H. Burkett, San Diego, CA (US); Arakady Kokish, Los Gatos, CA (US); Chicheng Wang, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/475,106

(22) Filed: Dec. 30, 1999

(51) Int. Cl.[7] .......................... A61F 2/06; A61M 29/00
(52) U.S. Cl. ...................................... 623/1.11; 606/200
(58) Field of Search ........................ 623/1.11; 606/200, 606/108, 191, 194, 195, 198; 604/96, 97.01, 97.02, 104, 105, 106, 107, 108

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |

(List continued on next page.)

FOREIGN PATENT DOCUMENTS

| | | |
|---|---|---|
| EP | 0 427 429 A2 | 5/1991 |
| EP | 0 472 334 A1 | 2/1992 |
| WO | WO92/03097 | 3/1992 |
| WO | WO96/01591 | 1/1996 |
| WO | WO97/17100 | 5/1997 |
| WO | WO 99/16382 | 4/1999 |
| WO | WO99/23976 | 5/1999 |

Primary Examiner—Michael J. Milano
Assistant Examiner—Vy Q. Bui
(74) Attorney, Agent, or Firm—Fulwider Patton Lee & Utecht, LLP

(57) ABSTRACT

A catheter apparatus includes a lesion dilating member disposable at a lesion position in a vessel (e.g. a patient's artery) which is dilatable to open the vessel at the lesion position. An emboli-capturing assembly having a perfusion member and filter is displaced downstream from the lesion dilating member to capture embolic debris released in the fluid flow. The perfusion member may illustratively have peaks and channels formed between adjacent peaks which cooperate with the filter to create trapping pockets that capture embolic debris. The filter may be made from any flexible and porous material with dimensions to pass the fluid and block the emboli. The perfusion member is thereafter deflated to provide for emboli retention in the perfusion member.

17 Claims, 5 Drawing Sheets

U.S. PATENT DOCUMENTS

| | | | |
|---|---|---|---|
| 5,092,839 A | 3/1992 | Kipperman | |
| 5,100,425 A | 3/1992 | Fischell et al. | |
| 5,102,415 A | 4/1992 | Guenther et al. | |
| 5,108,419 A | 4/1992 | Reger et al. | |
| 5,152,777 A | 10/1992 | Goldberg et al. | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,330,482 A | 7/1994 | Gibbs et al. | |
| 5,350,398 A | 9/1994 | Pavcnik et al. | |
| 5,370,657 A | 12/1994 | Irie | |
| 5,383,887 A | 1/1995 | Nadal | |
| 5,421,832 A | 6/1995 | Lefebvre | |
| 5,490,859 A | 2/1996 | Mische et al. | |
| 5,496,277 A | 3/1996 | Termin et al. | |
| 5,496,330 A | 3/1996 | Bates et al. | |
| 5,501,694 A | 3/1996 | Ressemann et al. | |
| 5,549,626 A | 8/1996 | Miller et al. | |
| 5,601,595 A | 2/1997 | Smith | |
| 5,626,605 A | 5/1997 | Irie et al. | |
| 5,634,942 A | 6/1997 | Chevillon et al. | |
| 5,649,953 A | 7/1997 | Lefebvre | |
| 5,662,671 A | 9/1997 | Barbut et al. | |
| 5,669,933 A | 9/1997 | Simon et al. | |
| 5,681,347 A | 10/1997 | Cathcart et al. | |
| 5,695,518 A | 12/1997 | Laerum | |
| 5,695,519 A | 12/1997 | Summers et al. | |
| 5,720,764 A | 2/1998 | Naderlinger | |
| 5,725,550 A | 3/1998 | Nadal | |
| 5,746,767 A | 5/1998 | Smith | |
| 5,755,790 A | 5/1998 | Chevillon et al. | |
| 5,769,816 A | 6/1998 | Barbut et al. | |
| 5,772,674 A | 6/1998 | Nakhjavan | |
| 5,779,716 A | 7/1998 | Cano et al. | |
| 5,792,145 A | 8/1998 | Bates et al. | |
| 5,792,156 A | 8/1998 | Perouse | |
| 5,792,157 A | 8/1998 | Mische et al. | |
| 5,795,322 A | 8/1998 | Boudewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,650 A | 11/1998 | Imran | |
| 5,836,868 A | 11/1998 | Ressemann et al. | |
| 5,846,251 A | 12/1998 | Hart | |
| 5,846,260 A | 12/1998 | Maahs | |
| 5,848,964 A | 12/1998 | Samuels | |
| 5,868,708 A | 2/1999 | Hart et al. | |
| 5,876,367 A | 3/1999 | Kaganov et al. | |
| 5,897,567 A | 4/1999 | Ressemann et al. | |
| 5,910,154 A | 6/1999 | Tsugita et al. | |
| 5,911,734 A | 6/1999 | Tsugita et al. | |
| 5,941,896 A | 8/1999 | Kerr | |
| 5,954,741 A * | 9/1999 | Fox | 606/198 |
| 5,954,745 A * | 9/1999 | Gertler et al. | 606/200 |
| 5,968,071 A | 10/1999 | Chevillon et al. | |
| 5,976,172 A | 11/1999 | Homsma et al. | |
| 5,980,555 A | 11/1999 | Barbut et al. | |
| 5,989,281 A | 11/1999 | Barbut et al. | |
| 6,001,118 A | 12/1999 | Daniel et al. | |
| 6,013,093 A | 1/2000 | Nott et al. | |
| 6,053,932 A * | 4/2000 | Daniel et al. | 606/200 |
| 6,231,588 B1 * | 5/2001 | Zadno-Azizi | 606/200 |
| 6,336,934 B1 * | 1/2002 | Gilson et al. | 606/200 |

* cited by examiner

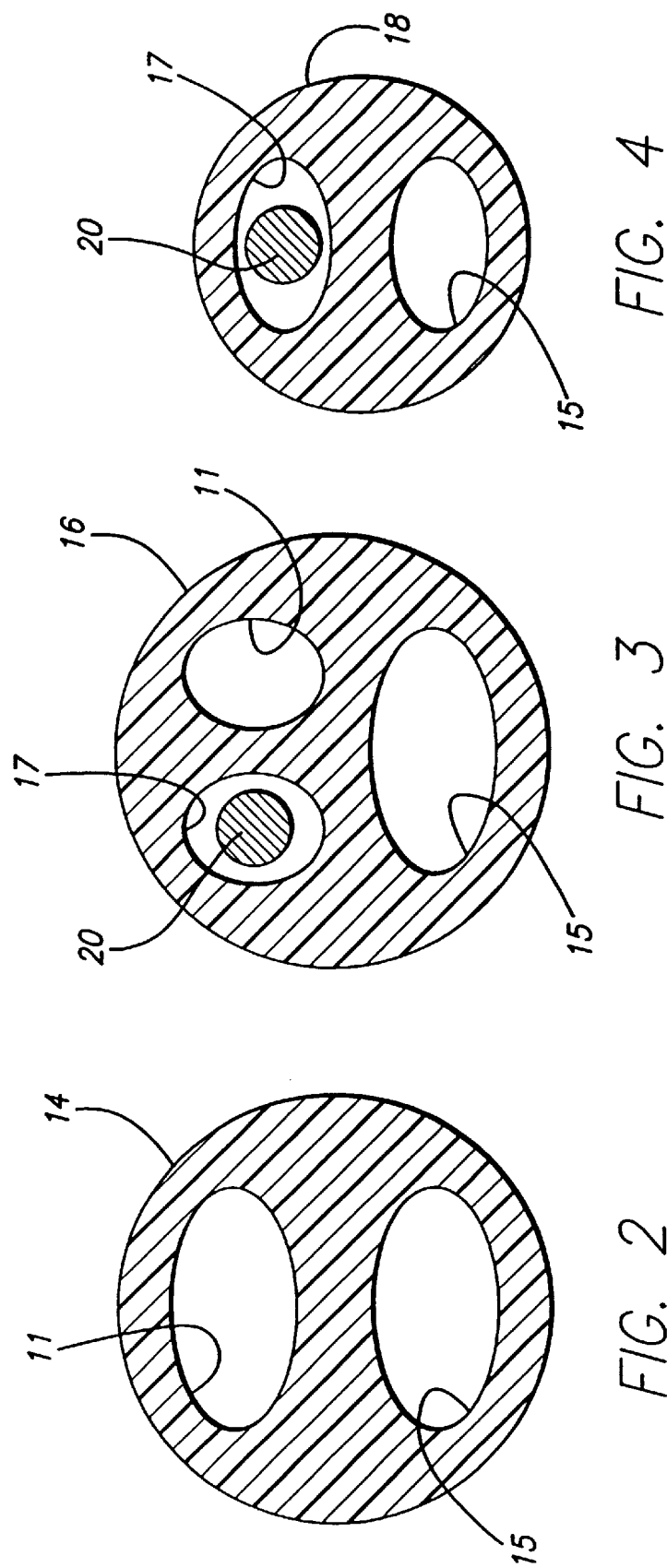

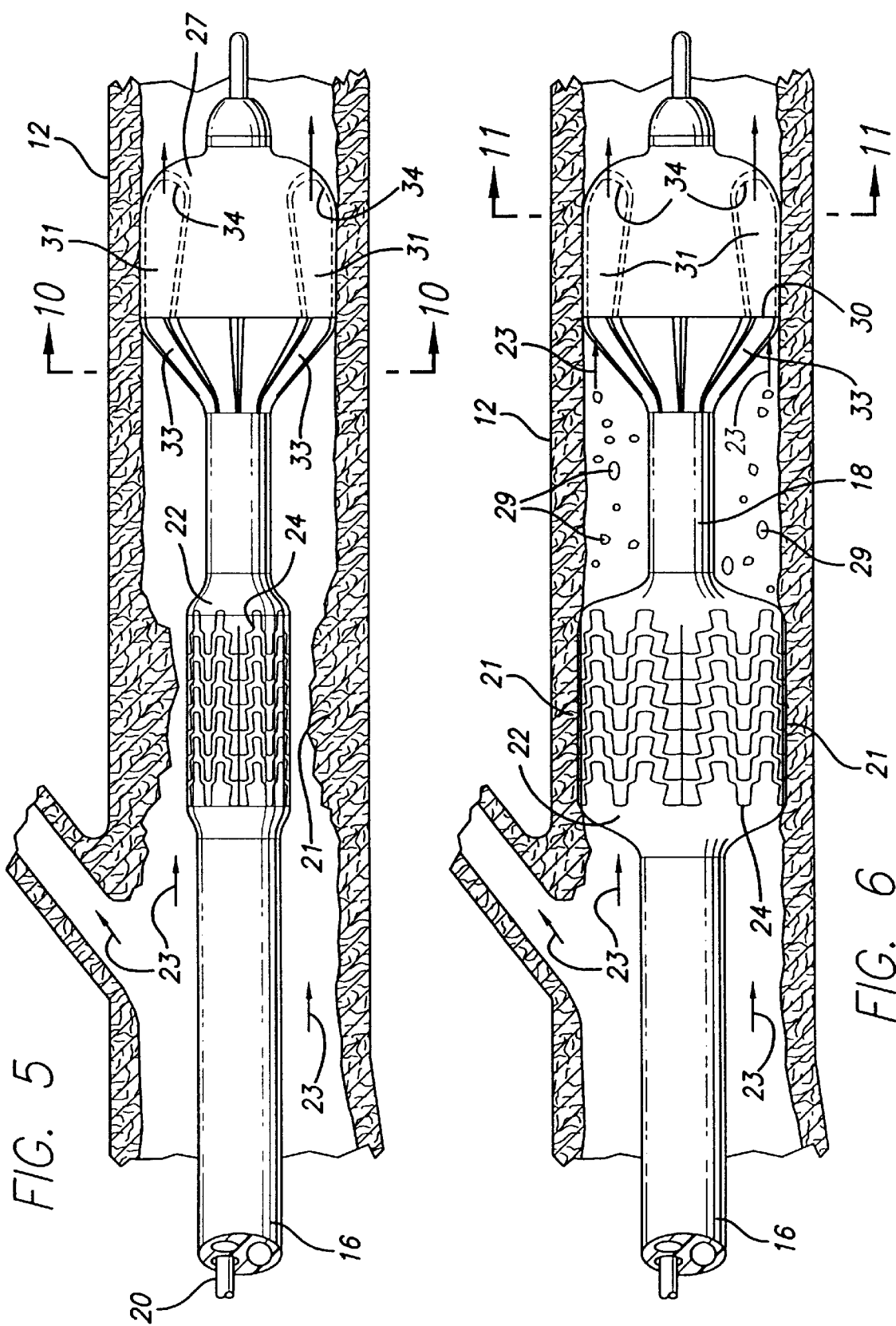

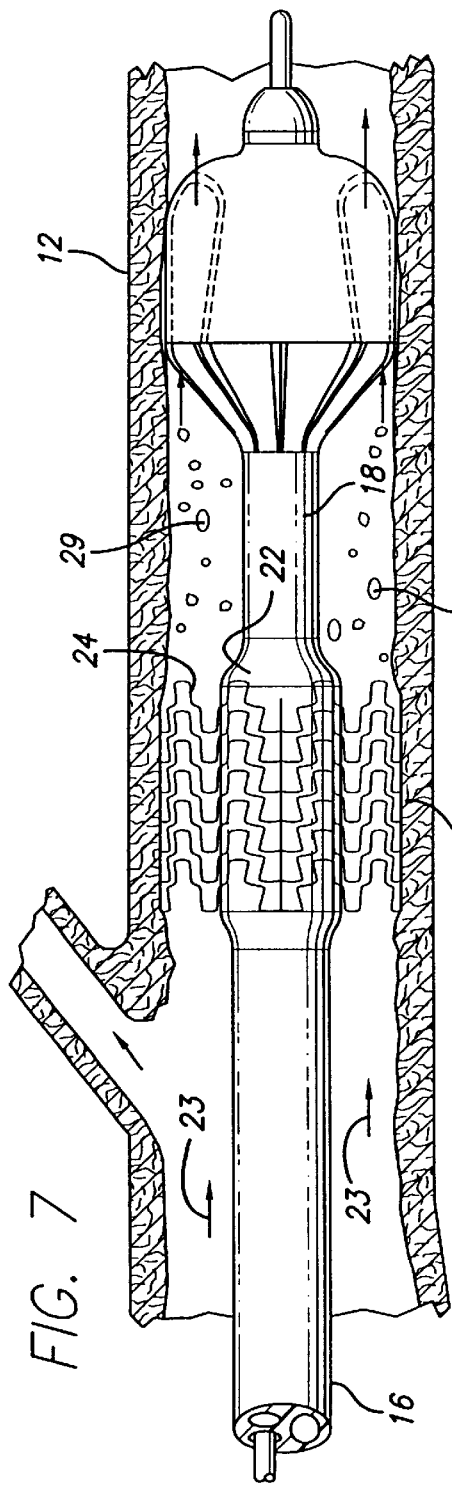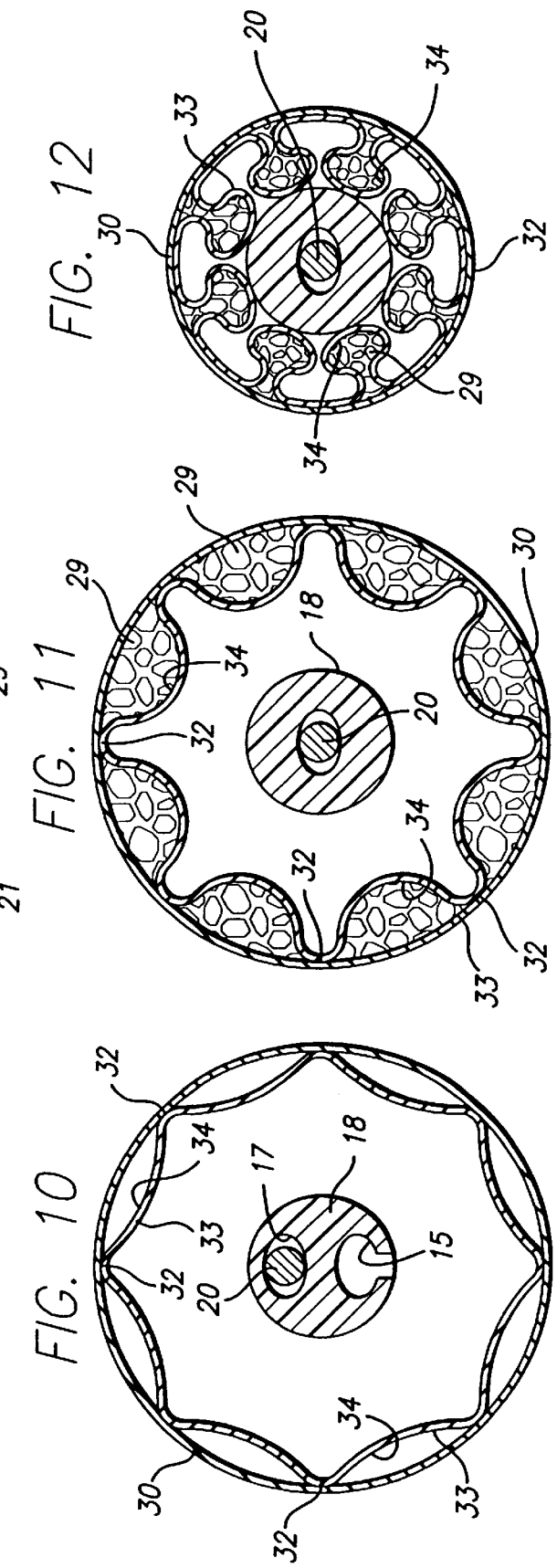

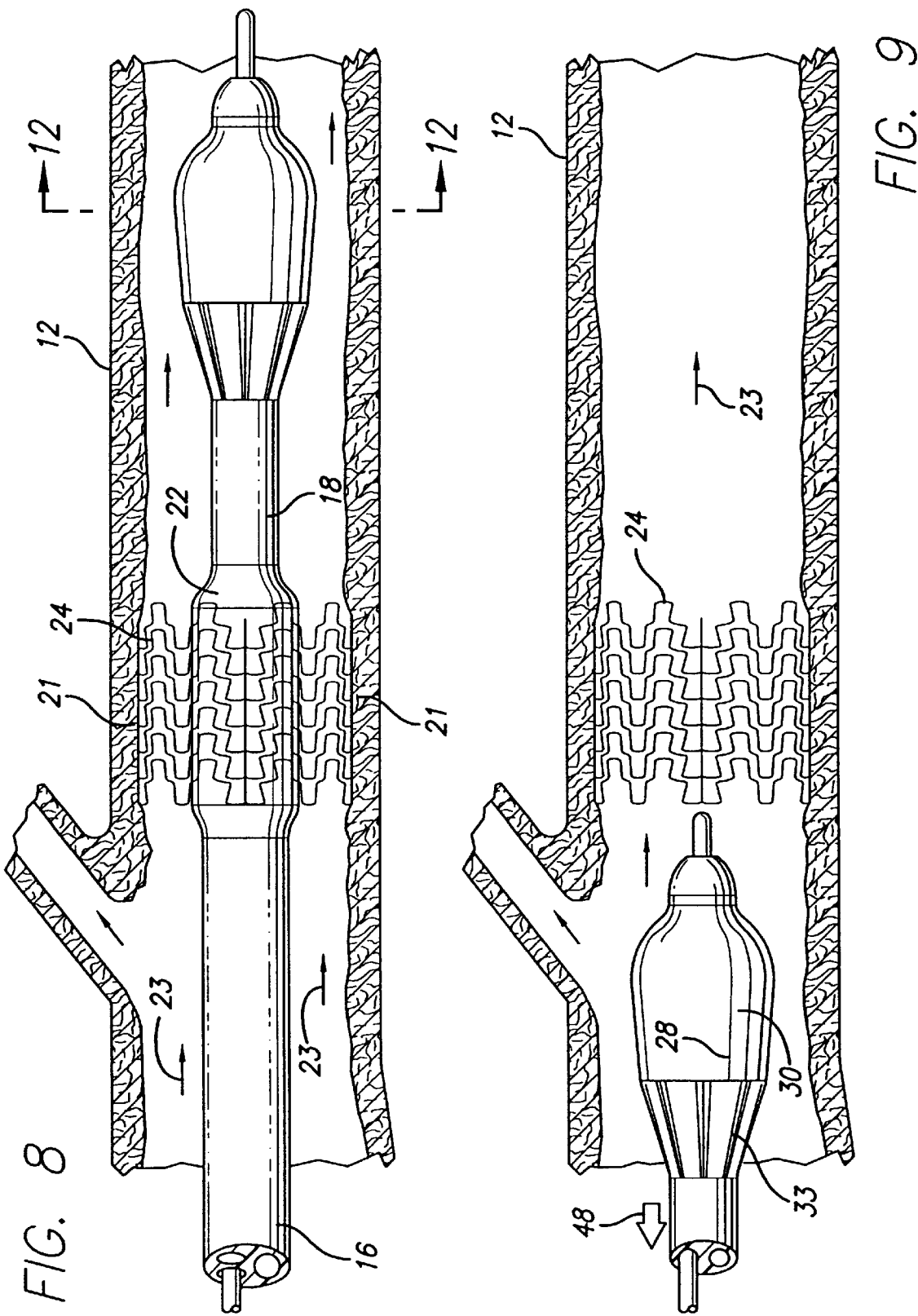

CATHETER APPARATUS FOR TREATING OCCLUDED VESSELS AND FILTERING EMBOLIC DEBRIS AND METHOD OF USE

BACKGROUND OF THE INVENTION

This invention relates to an apparatus for, and a method of, treating occluded vessels (e.g. an artery) and capturing friable emboli which may break away from the lesion in the vessel during the interventional procedure. The apparatus and method of the present invention are especially useful when performing carotid interventional procedures in order to prevent emboli or debris from entering and occluding downstream blood vessels leading to the brain which, if blocked, may cause a stroke. However, the system and method of this invention can be adapted by a person of ordinary skill in the art for use in numerous other vascular interventional procedures.

In recent years, numerous procedures have been adapted for expanding blood vessels (e.g. arteries), at the positions of lesions in the blood vessels, so that blood can flow through the blood vessels without obstruction from the lesions. In the process of expanding such blood vessels at the positions of the lesions, emboli may become detached from the lesions and enter the bloodstream and subsequently migrate through the patient's vasculature to occlude small diameter vessels which supply oxygenated blood to sensitive organs such as the brain, where such blockage may induce trauma.

Procedures have also been adapted in recent years for preventing embolic debris from flowing through the vessels in the direction of the blood flow. For example, filters have been provided for trapping the emboli. When lesions develop in the carotid artery of a patient, the placement of a filter in the patient's vasculature can somewhat reduce the movement of the emboli to the blood vessels supplying the patient's brain, thereby preventing strokes from occurring.

Such filters are usually delivered in a collapsed position through the patient's vasculature and are then expanded once in place in the patient's blood vessel to trap the emboli. After emboli have been trapped, the filter is collapsed to remove the filter (with the trapped emboli) from the vessel. However, it is possible for some of the trapped emboli to escape from the filter during the time that the filter is being collapsed and/or removed from the blood vessel after being collapsed. When an interventional procedure is being performed in a carotid artery, even a trace release of emboli can be devastating. For this reason, attempts to treat lesions in the carotid arteries have been somewhat limited due to the danger presented if all of the embolic debris is not collected during the procedure.

Therefore, in light of the above, it would be desirable for an apparatus and method which can be utilized to treat an occluded vessel and trap any emboli that may be formed during the vascular procedure. Such an apparatus and method must also prevent the emboli from escaping from the filter during the time that the filter is being collapsed and/or removed from the blood vessel (e.g. the carotid arteries). Such a device or method should be easy and safe to deploy, and be easily removed from the vasculature with minimal adverse impact or immulogical response to the patient.

SUMMARY OF THE INVENTION

The present invention addresses the above-mentioned needs by providing a catheter apparatus which can be used to treat an occluded vessel and trap any embolic debris which may be released into the bloodstream during the procedure. The catheter apparatus includes both a lesion dilating member (the interventional device) and an emboli capturing filter assembly which can be simultaneously introduced into the patient's vasculature. In one preferred embodiment, the lesion dilating member is an expandable member, such as a dilatation balloon, which is disposable at the lesion position in the vessel (e.g. a patient's artery) and dilatable to open the vessel. The emboli capturing filter assembly can be formed from a perfusion member (a balloon) which has a number of channels formed at its outer surface and filter material placed over the outer surface of the balloon. The emboli-capturing assembly is distal to, and placed downstream from, the lesion dilating member to capture, when the perfusion member is expanded, any emboli released into the bloodstream of the vessel. The emboli will be retained within a reservoir formed on the emboli capturing assembly until the procedure is completed. Thereafter, the perfusion member (with the trapped embolic debris) can be deflated and removed from the vasculature.

The perfusion member may be any one of a number of conventional perfusion balloons known in the art. Perfusion balloons are sometimes utilized during angioplasty and other interventional procedures when blood perfusion past an inflated dilatation balloon is required. A conventional perfusion balloon usually has a number of channels formed along the balloon's outer surface to create conduits to allow blood to pass through when the perfusion balloon is inflated within a blood vessel. The perfusion balloon may have any one of a number of different cross-sectional shapes, such as a star-shape, and the channels may be straight or spiral. The shape of the balloon and the number of channels formed on the perfusion balloon should ensure that adequate blood flow past the inflated balloon is achieved and maintained throughout the procedure.

A filtering material is placed over the outer surface of the perfusion member to create a "pocket" with each channel of the perfusion member and traps any embolic debris that may pass through the inlet of the channel. This filtering coverage starts distally from the proximal end of the perfusion member and terminates at the distal end of the perfusion member to create a deep "pocket" or "reservoir" which allows for the free flow of blood but catches any emboli which may be released in the bloodstream. After the perfusion member is completely expanded against the vessel wall, blood and embolic debris enters the "pocket" formed between the filter and the perfusion member.

The perfusion member may illustratively have peaks and channels formed between adjacent peaks. The depth of the channels at the center region of the perfusion member is usually less than at the distal end of the perfusion member. In one preferred embodiment, the perfusion member has a star-shaped cross-section which creates individual channels that cooperate with the filtering material to create the filtering "pockets" which receive the blood and any embolic debris released into the bloodstream. The size and depth of the channel at the center region are designed to be shallower than the channel as it proceeds distally along the perfusion member. The smaller opening of the channel where the coverage of the filter begins permits sufficient fluid flow into the channel with the larger or deeper portion of the channel at the distal end of the perfusion balloon forming the reservoir for capturing and retaining the embolic debris. When deflated, the perfusion member provides for retention of the trapped emboli in the perfusion member. Due to the unique construction of the shallower channel at the inlet opening of the perfusion member, any trapped emboli in the distal reservoir portion is less likely to be discharged out of the smaller channel opening once the perfusion member is deflated. The filtering material may be made from any flexible and porous material with dimensions to allow fluid (blood) to pass through and block the embolic debris.

In use, the catheter apparatus is initially disposed in a vessel with the lesion dilating member juxtaposed to the lesion and the emboli-capturing assembly positioned downstream from the lesion in the fluid flow direction. The perfusion member is initially inflated to deploy the filtering portion of the catheter and the lesion dilating member is then dilated to expand the vessel at the lesion position. The lesion dilating member is thereafter deflated to ensure that any emboli from the lesion which may be trapped against the inflated dilating member is allowed to travel with the blood flow into the trapping "pocket" of the perfusion member. The perfusion member is thereafter deflated and removed (with the trapped emboli) from the patient's vasculature.

Other features and advantages of the present invention will become more apparent from the following detained description of the invention, when taken in conjunction with the accompanying exemplary drawings.

BRIEF DESCRIPTION OF THE DRAWINGS

FIG. 2 is a sectional view of the catheter at a first position in the apparatus of FIG. 1 and is taken substantially along line 2—2 of FIG. 1.

FIG. 3 is a sectional view of the catheter at a second position in the apparatus of FIG. 1 and is taken substantially along line 3—3 of FIG. 1.

FIG. 4 is a sectional view of the catheter at a third position in the apparatus of FIG. 1 and is taken substantially along line 4—4 of FIG. 1.

FIG. 5 is a fragmentary schematic view of the apparatus of FIG. 1 with the catheter advanced into the vessel so that the lesion dilating member is juxtaposed to a lesion and the emboli-capturing assembly is displaced from the lesion in the direction of the fluid flow with the perfusion member inflated.

FIG. 6 is a fragmentary schematic view similar to that shown in FIG. 5 but shows the lesion dilatable member dilated to treat the stenosis.

FIG. 7 is a fragmentary schematic view similar to that shown in FIG. 6 but shows the lesion dilatable member deflated with the perfusion member inflated to capture emboli.

FIG. 8 is a fragmentary schematic view similar to that shown in FIGS. 5 and 6 but with the lesion dilatable member and the perfusion member deflated.

FIG. 9 is a fragmentary schematic view similar to that shown in FIG. 7 but with the lesion dilatable member and the emboli-capturing assembly withdrawn through the vessel to a position in front of the lesion in the direction of fluid flow through the vessel.

FIG. 10 is a sectional view taken substantially along line 10—10 of FIG. 5 and shows the center region of the perfusion member with the perfusion member inflated.

FIG. 11 is a sectional view taken substantially along line 11–12 of FIG. 6 and shows the distal end of the perfusion member with the perfusion member inflated; and FIG. 12 is a sectional view taken substantially along line 12—12 of FIG. 7 and shows the perfusion member in deflated form.

DETAILED DESCRIPTION OF THE PREFERRED EMBODIMENTS

Figure 1:
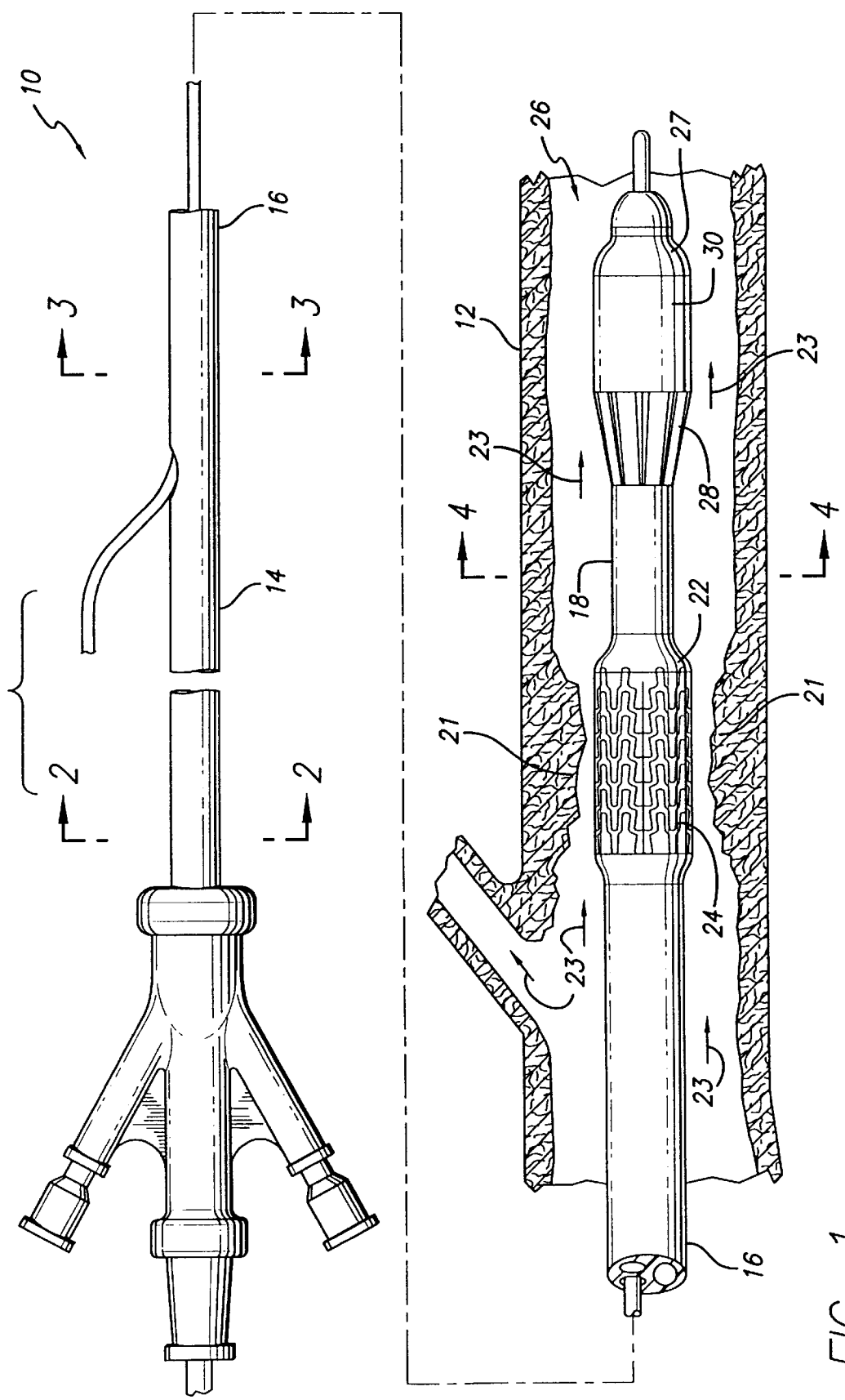
FIG. 1 is a schematic view of a catheter apparatus which includes a lesion dilatable member (e.g. expandable balloon and stent) and an emboli-capturing assembly (a perfusion member and filter) for expanding a vessel (e.g. an artery) at the position of a lesion and trapping emboli produced during the vessel expansion.

A preferred embodiment of a catheter apparatus for treating an occluded vessel and capturing embolic debris in a blood vessel, generally indicated at 10, is shown in the drawings. The catheter 10 is constructed to extend through a vessel 12 such as a patient's artery. The catheter 10 may include a dual-lumen tubing 14 (FIG. 2) at the proximal end. The dual-lumen tubing 14 may be connected to a tri-lumen tubing 16 (FIG. 3) at its distal end. At the distal end of the tri-lumen tubing 16, a dual-lumen tubing 18 may be provided (FIG. 4). The dual-lumen tubings 14 and 18 and the tri-lumen tubing 16 are known in the art. The dual-lumen tubing 14 includes a pair of inflation lumens 11 and 15 which are used for inflating and deflating the lesion dilating member 22 and perfusion member 28 described below. Alternatively, a tri-lumen tubing may be used throughout the length of the catheter 10. A guide wire 20 may extend through the guidewire lumen 17 extending through the tri-lumen tubing 16 and the dual-lumen tubing 18. The guide wire 20 may illustratively have a diameter of approximately fourteen thousandths of an inch (0.014").

The catheter 10 includes a lesion dilating member (e.g. inflatable balloon) 22 which is utilized in performing the interventional procedure. The lesion dilating member 22 is known in the art. It is constructed to be disposed at the position of a lesion 21 in the vessel 12 (e.g. a carotid artery) and to expand the vessel, when dilated, to reduce the blockage in the vessel at the position of the lesion. The expansion of the vessel 12 at the position of the lesion 21 may be seen from a comparison of FIGS. 5 and 6. In this way, fluid (e.g. blood) can flow through the vessel 12 at the position of the lesion 21 without obstruction. The lesion dilating member 22 is thereafter deflated when it is desired to remove the balloon from the vessel 12. The flow of the fluid through the vessel 12 is indicated by arrows 23 in the drawings.

In the embodiment disclosed herein, the lesion dilating member 22 is utilized with a device known as stent 24 which is implanted in the artery 12 to reduce the likelihood of the occurrence of an abrupt reclosure of the stenosed region and to strengthen the area which undergoes the angioplasty procedure. Stents are usually delivered in a compressed condition to the target location and then are deployed into an expanded condition to support the vessel and help maintain it in an open position. The stent is usually crimped tightly onto a delivery catheter and is transported through the patient's vasculature. The stent is extendible upon application of a controlled force, in this case through the inflation of the balloon portion of the lesion dilating member 22, which expands the compressed stent 24 to a larger diameter to be implanted within the artery 12 at the target location. Although the stent 24 shown in this embodiment requires application of a controlled force to expand it within the artery, the stent could also be made from a self-expanding type formed from, for example, shape-memory metals or superelastic nickel titanium (NiTi) alloys, which will automatically expand from a compressed to an expanded state, thereby eliminating the need for an expandable balloon.

In the present embodiment, the lesion dilating member 22 causes the lesion 21 to compress against the wall of the vessel 12. Again, as the balloon portion of the lesion dilating member expands, so does the stent 24 which, as is shown in FIGS. 6–9, contacts the stenosis to compress the plaque build-up and increase the diameter of the blood vessel 12.

An emboli-capturing assembly, generally indicated at 26 in FIG. 1, is located on the catheter 12 at a position distal from the lesion dilating member 22. The emboli-capturing assembly 26 includes a perfusion member (e.g. balloon)28 and a filter 30 attached to the outer surface of the perfusion member.

The filter 30 is attached to the perfusion member 28, preferably by tightly bonding the filter onto the outer surface of the perfusion member by adhesives or other bonding method. In this particular embodiment, the coverage of the filter 30 starts from approximately the middle or central section 25 of the perfusion member 28 and terminates at the distal end 27 of the perfusion member. The channels 33 of perfusion member 28 and the filter 30 are disposed relative to each other, with the filter bonded to the perfusion member to define a trapping "pocket" 31 (FIG. 10) which extends along the length of the perfusion member to capture embolic debris 29 in the bloodstream.

The perfusion member 28 is provided with a series of undulations providing variations in depth at progressive annular positions. The number of undulations can be variable. For example, the number of undulations may be eight (8) as shown in FIG. 10. The undulations may be defined by peaks 32 and channels 33 between the peaks as schematically shown in FIG. 10. As will be seen, the peaks 32 contact the wall 13 of the vessel. The distal end 27 of the perfusion member 28 may have undulations defined by peaks 32 and channels 33. This is illustrated schematically in FIG. 11.

The depth of the channel, i.e. the distance from the peak 32 to the bottom 34 of the channel 33, may be relatively small at the center section 25 of the perfusion member 28 with the distance from the peaks 32 to the bottom of the channels 33 being relatively larger at the distal end 27 of the perfusion member. This may be seen from a comparison between the perfusion member 28 as shown in FIGS. 10 and 11. In this way, the perfusion member 28 provides relatively shallow channels at the center section 25 of the perfusion member which are adequate to receive (blood) along with any embolic debris 29 released into the fluid. This allows the fluid and the embolic debris 29 to flow into each inlet opening 35 at the center section 25 of the perfusion balloon and enter into the "pocket" 31 created by the filter 30 and each channel 33. Other forms of perfusion members 28 such as spiral members (e.g. balloons) and stud radiation members (e.g. balloons) can also be used. The channels at the distal end 27 of the perfusion member 28 and in the filter 30 are relatively deep to form "reservoirs" 34 for trapping and holding the embolic debris 29.

The filter 30 extends across the vessel 12 to allow fluid to pass through while blocking and trapping the embolic debris 29. The filter 30 may be made from any film which is flexible and porous and which has a pore size to pass blood and block the emboli. Certain commercially available materials such as a material designated by the trademark Goretex are suitable filtration membrane materials. The filter 30 can also be made from elastomers with open cell foams.

The lesion dilating member 22, the perfusion member 28 and the filter 30 are pre-folded. The catheter 12 is first advanced so that the lesion dilating member 22 is juxtaposed to the lesion 21 in the vessel as shown in FIG. 1 and the perfusion member 28 and the filter 30 are located past the position of the lesion in the direction of the fluid flow also as shown in FIG. 1. The length of the dual-lumen tubing 18 can be varied as needed without departing from the spirit and scope of the present invention. The perfusion member 28 is then dilated to the configuration shown schematically in FIG. 5. This opens the perfusion member 28 and fully opens the filter 30.

As shown in FIG. 6, the lesion dilating member 22 is thereafter expanded (along with the stent 24) to open the vessel 12 to the flow of fluid at the position of the lesion 21. Since the metal struts of the stent 24 may cut into the stenosis lesion 21 as it is expanded, emboli may be generated at this time. After the vessel 12 has been opened at the position of the lesion 21 as shown schematically in FIG. 6, the lesion dilating member 22 is deflated. This will cause the fluid (e.g. blood) to resume its flow into the artery. The deflation of the lesion dilating member 22 is shown schematically in FIG. 6. The resumption of the blood flow in the area of the stenosis lesion 21 causes any emboli which may have been trapped against the outer surface of the lesion dilating member to be swept into the blood flow to be ultimately trapped in the emboli-capturing assembly 26.

Any embolic debris 29 generated from the expansion of the lesion dilating member 22 will flow downstream with the blood into inlet openings 35 of the channels 33 of the perfusion member 28, this being the only open area. The fluid (blood) will be permitted to flow through the filter 30 to reach blood vessels distal to the inflated perfusion member 28 in order to maintain a sufficient flow of oxygenated blood to downstream organs and tissue. However, emboli 29 will be blocked from passing through the filter 30. The emboli will thus remain in the deep reservoirs 34 (FIG. 6) formed at the distal end of the perfusion member 28.

A period of time is allowed to pass to ensure that all of the embolic debris 29 is collected in the deep reservoir 34 at the distal end of the perfusion member 28 (FIG. 7). The perfusion member 28 is then deflated (FIG. 8). The deflation of the perfusion member 28 causes the shallow portion of the channels at the center section 25 to collapse before the deeper distal portion of the channel. Since these channels are deeper at the distal end than the channels shown in FIG. 11, embolic debris 29 remains trapped in the deeper portion of the channel. The dilating balloon 22 and the perfusion balloon 28 may then be pulled into a sheath (not shown) without losing any of the embolic debris 29 which may otherwise flow through the inlet openings of the channels 33 of the perfusion member 28. The sheath is then removed from the vessel 12. The removal of the catheter 10 from the vessel 12 is indicated schematically by an arrow 48 in FIG. 9.

The lesion dilating member 22 has been shown in the figures as an expandable member, such as a balloon, and a stent which performs the interventional procedure. However, it is possible to use a single expandable member, such as a dilatation balloon, which can be utilized to perform a simple angioplasty procedure. While a convention stent has been described in conjunction with the present invention, it is possible to use a self-expanding stent to perform the interventional procedure as well. If a self-expanding stent is utilized, a restraining sheath would be required to be placed over the collapsed stent when the catheter is positioned within the patient's vasculature. Thereafter, once the stent is in proper position in the artery, the restraining sheath can be retracted to expose the self-expanding stent which will then expand radially outward to open the occluded portion of the artery.

Various catheter components of the present invention can be made from conventional materials utilized in angioplasty catheters and other well-known catheters in the art. For example, the catheter can be made from a polymeric material such as a low or medium molecular weight polyolesin, examples of which include PE, EVAc, EVA, and IONOMERS. Any other plastic materials or blend of materials, including crosslinked materials and composites, may also be suitable.

The perfusion member (balloon) illustrated in the drawings utilizes a conventional perfusion balloon well-known in the art. However, it will be readily apparent to one skilled in the art that a modified balloon could also be made in accordance with the present invention. For example, a perfusion member can be utilized with specially designed channels which extend proximally to distally with shallower channels in the proximal portion of the balloon with larger channels at the distal end of the balloon. Moreover, the coverage of the filtering material could start from the proximal end of the balloon where the inlet opening and channel are shallower than the distal portion of the balloon which forms the "reservoir" portion of the emboli-capturing assembly. The number of channels and the size (depth and width) and shape of the channels can be varied accordingly without departing from the spirit and scope of the present invention. Additionally, a longer perfusion balloon can be used ti create a longer "pocket" for trapping the emboli. By creating a longer pocket, emboli pushed deep into the reservoir portion of the pocket will have a more difficult time migrating back towards the inlet opening as the perfusion member being collapsed.

The catheter apparatus described above has certain important advantages. It provides for the retention of emboli in the perfusion member during the interventional procedure. It also provides for proper retention of the emboli as the perfusion member is being collapsed and withdrawn from the vessel. In this way, the present invention helps prevent a patient from having a stroke during and after intervention procedures. The present invention is also advantageous in that it is simple in construction and easy to operate.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

What is claimed:

1. A catheter apparatus for treating a lesion-blocked vessel and capturing emboli flowing through the vessel, comprising:
   a lesion dilating member for disposition in the vessel at the position of the lesion blockage, the lesion dilating member being expandable to open the vessel at the position of the lesion, and
   a perfusion member and filter for disposition in the vessel at a position displaced from the lesion, the perfusion member having proximal and distal ends with the filter attached to the outer surface of the perfusion member at a location distal to the proximal end of the perfusion member, wherein
   the outer surface of the perfusion member has a plurality of annularly spaced peaks and channels formed between adjacent peaks and the filter to allow the flow of a fluid to pass through the channels and the filter is made from a material which allows the fluid to pass but not emboli.

2. The catheter apparatus of claim 1 wherein the distance between the peaks and the bottoms of the channels at the start of the coverage of the filter is less than the distance between the peaks and the bottoms of the channels at the distal end of the perfusion member.

3. The catheter apparatus of claim 1 wherein the perfusion member is expandable from a collapsed to an expanded position.

4. The catheter apparatus of claim 1 wherein the perfusion member is an expandable member.

5. The catheter apparatus of claim 4 wherein the expandable member is a balloon.

6. The catheter apparatus of claim 1 wherein the filter coverage starts substantially near the center of the perfusion member.

7. The catheter apparatus of claim 1 wherein each channel of the perfusion member has a particular depth.

8. The catheter apparatus of claim 7 wherein the depth of the channel varies along the length of the perfusion member.

9. An emboli-capturing device for capturing emboli released into the fluid of a body vessel, comprising:
   a perfusion member having proximal and distal ends and a filter attached to the outer surface of the perfusion member at a location distal to the proximal end of the perfusion member, wherein
   the outer surface of the perfusion member has a plurality of annularly spaced peaks and channels formed between adjacent peaks and the filter to allow the flow of a fluid to pass through the channels and the filter is made from a material which allows the fluid to pass but not emboli.

10. The emboli-capturing device of claim 9 wherein the distance between the peaks and the bottoms of the channels at the start of the coverage of the filter is less than the distance between the peaks and the bottoms of the channels at the distal end of the perfusion member.

11. The catheter apparatus of claim 9 wherein the perfusion member is expandable from a collapsed to an expanded position.

12. The catheter apparatus of claim 9 wherein the perfusion member is an expandable member.

13. The catheter apparatus of claim 12 wherein the expandable member is a balloon.

14. The catheter apparatus of claim 9 wherein the filter coverage starts substantially near the center of the perfusion member.

15. The catheter apparatus of claim 9 wherein each channel of the perfusion member has a particular depth.

16. The catheter apparatus of claim 9 wherein the depth of the channel varies along the length of the perfusion member.

17. The catheter apparatus of claim 9 wherein the filter is bonded to the peaks of the perfusion member.

* * * * *

UNITED STATES PATENT AND TRADEMARK OFFICE
CERTIFICATE OF CORRECTION

PATENT NO.    : 6,511,503 B1
DATED         : January 28, 2003
INVENTOR(S)   : David H. Burkett et al.

It is certified that error appears in the above-identified patent and that said Letters Patent is hereby corrected as shown below:

<u>Title page,</u>
Item [75], Inventors, change "Arakady", to read -- Arkady --.

Signed and Sealed this

Fifteenth Day of July, 2003

JAMES E. ROGAN
*Director of the United States Patent and Trademark Office*